(12) United States Patent
Rosenzweig et al.

(10) Patent No.: US 10,451,587 B2
(45) Date of Patent: Oct. 22, 2019

(54) METHODS, SYSTEMS AND COMPUTER PROGRAM PRODUCTS FOR ESTIMATING SHEAR WAVE SPEED USING STATISTICAL INFERENCE

(71) Applicant: Duke University, Durham, NC (US)

(72) Inventors: Stephen J. Rosenzweig, Seattle, WA (US); Ned C. Rouze, Durham, NC (US); Brett C. Byram, Brentwood, TN (US); Mark L. Palmeri, Durham, NC (US); Kathryn R. Nightingale, Durham, NC (US)

(73) Assignee: Duke University, Durham, NC (US)

( * ) Notice: Subject to any disclaimer, the term of this patent is extended or adjusted under 35 U.S.C. 154(b) by 1043 days.

(21) Appl. No.: 14/801,007

(22) Filed: Jul. 16, 2015

(65) Prior Publication Data
US 2016/0018364 A1 Jan. 21, 2016

Related U.S. Application Data

(60) Provisional application No. 62/025,264, filed on Jul. 16, 2014.

(51) Int. Cl.
*G01N 29/07* (2006.01)
*G01N 29/44* (2006.01)
*A61B 8/08* (2006.01)

(52) U.S. Cl.
CPC ............ *G01N 29/07* (2013.01); *A61B 8/485* (2013.01); *G01N 29/449* (2013.01); *G01N 29/4472* (2013.01); *G01N 2291/02827* (2013.01); *G01N 2291/0422* (2013.01)

(58) Field of Classification Search
CPC .. G01N 29/07; G01N 29/449; G01N 29/4472; G01N 2291/02827; G01N 2291/0422; A61B 8/485
See application file for complete search history.

(56) References Cited

U.S. PATENT DOCUMENTS

| | | | | |
|---|---|---|---|---|
| 2004/0068184 A1* | 4/2004 | Trahey | ...................... | A61B 8/08 600/437 |
| 2008/0249408 A1* | 10/2008 | Palmeri | .................... | A61B 8/08 600/438 |
| 2013/0066204 A1* | 3/2013 | Fan | ...................... | A61B 8/0858 600/438 |

* cited by examiner

*Primary Examiner* — Bo Joseph Peng
(74) *Attorney, Agent, or Firm* — Myers Bigel, P.A.

(57) ABSTRACT

Methods, systems and computer program products for determining a mechanical parameter for a sample having a target region, include determining a prior probability density function that characterizes at least one physical property of the target region; generating a displacement of the sample in the target region to form a shear wave that propagates orthogonal to a direction of the displacement; transmitting tracking pulses in the target region; receiving corresponding echo signals for the tracking pulses in the target region at a plurality of lateral positions; estimating a propagation parameter of the shear wave in response to the echo signals and the prior probability density function using statistical inference; and determining at least one mechanical parameter of the target region based on the estimated propagation parameter.

12 Claims, 11 Drawing Sheets ary application claims priority to U.S. Provisional Application Ser. No. 62/025,264, filed Jul. 16, 2014, the disclosure of which are hereby incorporated by reference in its entirety.

METHODS, SYSTEMS AND COMPUTER PROGRAM PRODUCTS FOR ESTIMATING SHEAR WAVE SPEED USING STATISTICAL INFERENCE

RELATED APPLICATIONS

This application claims priority to U.S. Provisional Application Ser. No. 62/025,264, filed Jul. 16, 2014, the disclosure of which are hereby incorporated by reference in its entirety.

STATEMENT OF GOVERNMENT SUPPORT

This invention was made with government support under Grant No. 2 ROI EB-002132 awarded by the National Institutes of Health. The government has certain rights in the invention

FIELD OF THE INVENTION

The present invention relates to ultrasound imaging and analysis, and in particular, to determining mechanical parameters of a sample from estimated shear wave speeds using statistical inference.

BACKGROUND

Acoustic Radiation Force (ARF) shear wave elasticity imaging methods typically use a transverse propagation velocity of mechanical shear waves in materials to estimate mechanical properties of a sample, such as material elasticity constants. These techniques may be adapted into imaging systems to compute the local shear wave propagation velocity as a function of both axial and lateral position. The velocity may be calculated by estimating the differences in arrival times of the shear waves, either at different recording locations or from different excitation locations.

The velocity of the shear wave may, therefore, be estimated over a predefined lateral kernel or distance. The shear wave velocity is typically estimated using a time-of-flight based reconstruction technique that assumes a known direction of wave propagation and a homogeneous, isotropic tissue within the reconstruction kernel. Violations of these assumptions, however, can lead to biased shear wave speed estimates and image artifacts generated by reflected waves at the structural boundaries.

For example, acoustic radiation force (ARF) arises from a transfer of momentum from a sound wave to the medium through which it is traveling due to both absorption and scattering of the wave and is described by K. R. Nightingale, M. Palmeri, R. Nightingale, and G. Trahey, "On the feasibility of remote palpation using acoustic radiation force," J Acoust Soc Am, vol. 110, pp. 625-634, 2001 and G. R. Torr, "The Acoustic Radiation Force," Am. J. Phys., vol. 52, pp. 402-408, 1984.

$$\vec{F} = \frac{2\alpha \vec{I}}{c} \quad (1)$$

where $\alpha$ is the acoustic attenuation, I is the acoustic intensity, c is the speed of sound, and F is the force applied to the medium. SWEI utilizes this acoustic radiation force by applying ultrasonic pushing pulses that displace the tissue on the order of microns and tracking the propagation of the transverse wave that propagates away from the region of excitation.

A typical ARF-induced shear wave beam sequence begins with acquiring at least one conventional reference A-line in the region of interest (ROI), then applying the pushing pulse away from the ROI, and finally acquiring additional tracking A-lines. The response of the tissue is determined by estimating the displacement of the tissue between the pre-push reference and the post-push tracks. By observing how the shear wave propagates over multiple tracking lateral locations or multiple pushing lateral locations, it is possible to estimate the shear wave speed (SWS). Under the assumptions of homogeneous, linear elastic, incompressible, isotropic tissue, the shear modulus (G) is equal to three times the Young's modulus (E), and also equal to the density of the tissue ($\rho$) times the shear wave speed (S) squared (i.e., $G=3E=\rho g^2$). Thus, stiffer tissues have a higher shear wave speed than soft tissues, and by creating images of the shear wave speed, or derived shear or Young's modulus, the image contrast is related to the stiffness of the underlying tissue.

To estimate the SWS, the wave arrival time at each lateral and axial location is determined. Multiple methods exist for determining this wave arrival time, such as time-to-peak tissue displacement, time-to-peak tissue velocity, and cross-correlation between the displacement or velocity profiles at each lateral location. Typically, these wave arrival time estimates are then input into a time-of-flight algorithm, such as linear regression or random sample consensus, which fits the data to a model assuming a single shear wave speed across the lateral and axial reconstruction kernel. Specifically, linear regression is a maximum likelihood estimator that assumes a linear relationship between the arrival time at each location and the speed of the shear wave. In structured media, to obtain high resolution, small regression kernels are desired, but this leads to increased noise in the estimated SWS.

SUMMARY OF EMBODIMENTS OF THE INVENTION

In some embodiments, methods for determining a mechanical parameter for a sample having a target region, include determining a prior probability density function that characterizes at least one physical property of the target region; generating a displacement of the sample to form a shear wave that propagates orthogonal to a direction of the displacement; transmitting tracking pulses in the target region; receiving corresponding echo signals for the tracking pulses in the target region at a plurality of lateral positions; estimating a propagation parameter of the shear wave in response to the echo signals and the prior probability density function using statistical inference; and determining at least one mechanical parameter of the target region based on the estimated propagation parameter.

In some embodiments, the prior probability density function comprises acoustic radiation force impulse (ARFI) displacement magnitude and/or B-mode brightness.

In some embodiments, the prior probability density function comprises shear wave image data.

In some embodiments, estimating a propagation parameter comprises estimating a likelihood function based on the echo signals. The likelihood function may include a shear wave arrival time estimate that is based on the echo signals. The shear wave arrival time estimate may be based on a cross-correlation, a time-to-peak displacement, and/or a time-to-peak slope. The statistical inference may include a Bayesian probability based on the likelihood function and the prior probability density function.

In some embodiments, an ultrasound system for determining a mechanical parameter for a target region includes an ultrasound transducer array; a controller configured to control the ultrasound transducer to generate a tissue displacement in the target region, to transmit tracking pulses in the target region, and to receive corresponding echo signals for the tracking pulses in the target region at a plurality of the positions; and a signal analyzer configured to determine a prior probability density function that characterizes at least one physical property of the target region; to estimate a propagation parameter of the shear wave in response to the echo signals and the prior probability density function using statistical inference; and to determine at least one mechanical parameter of the target region based on the estimated propagation parameter.

In some embodiments, a computer program product for determining a mechanical parameter for a sample having a target region is provided. The computer program product includes a non-transient computer readable medium having computer readable program code embodied therein. The computer readable program code includes computer readable program code configured to determine a prior probability density function that characterizes at least one physical property of the target region; computer readable program code configured to generate a displacement of the sample in the target region to form a shear wave that propagates orthogonal to a direction of the displacement; computer readable program code configured to transmit tracking pulses in the target region; computer readable program code configured to receive corresponding echo signals for the tracking pulses in the target region at a plurality of lateral positions; computer readable program code configured to estimate a propagation parameter of the shear wave in response to the echo signals and the prior probability density function using statistical inference; and computer readable program code configured to determine at least one mechanical parameter of the target region based on the estimated propagation parameter.

BRIEF DESCRIPTION OF THE DRAWINGS

The accompanying drawings, which are incorporated in and constitute a part of the specification, illustrate embodiments of the invention and, together with the description, serve to explain principles of the invention.

DETAILED DESCRIPTION OF EMBODIMENTS OF THE INVENTION

Figure 1:
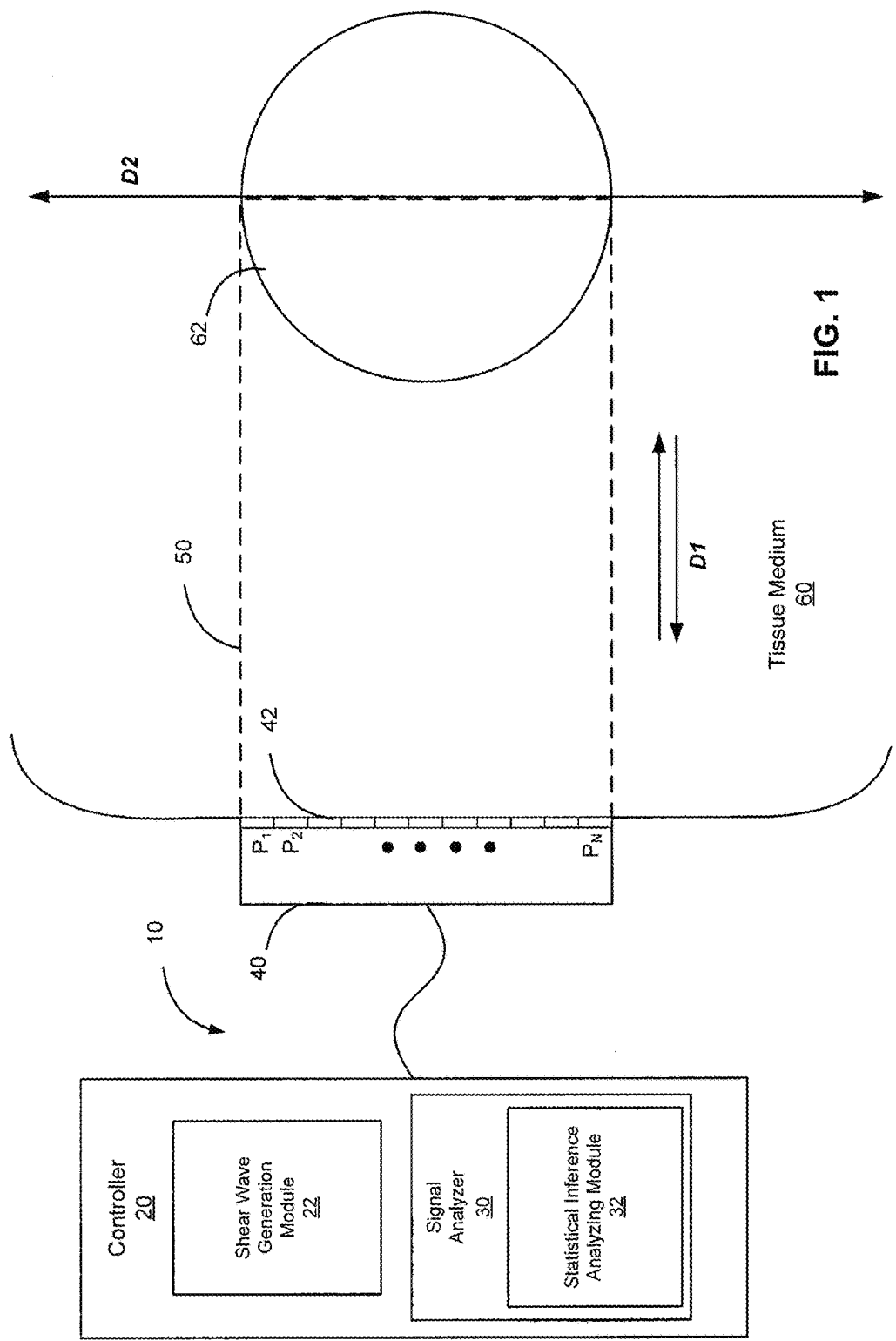
FIG. 1 is a schematic diagram of ultrasound systems, methods and computer program products according to some embodiments.

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. For example, the term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

The present invention is described below with reference to block diagrams and/or flowchart illustrations of methods, apparatus (systems) and/or computer program products according to embodiments of the invention. It is understood that each block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the function/act specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, the present invention may be embodied in hardware and/or in software (including firmware, resident software, micro-code, etc.). Furthermore, embodiments of the present invention may take the form of a computer program product on a computer-usable or computer-readable non-transient storage medium having computer-usable or computer-readable program code embodied in the medium for use by or in connection with an instruction execution system.

The computer-usable or computer-readable medium may be, for example but not limited to, an electronic, optical, electromagnetic, infrared, or semiconductor system, apparatus, or device. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM).

Embodiments according to the present invention are described herein with reference to the term "tissue." It will be understood that the term tissue can include biological materials, such as, blood, organs, vessels, and other biological objects found in a body. It will be further understood that embodiments according to the present invention may be applicable to humans as well as other species. Embodiments according to the present invention may also be utilized to image objects other than tissue.

It will be understood that the scope of the present invention includes, for example, two dimensional (2D) ultrasound imaging and 3D (or volumetric) ultrasound imaging. In addition, the components of the ultrasound imaging described herein may be packaged as a single unit or packaged separately and interconnected to provide the functions described herein.

Embodiments according to the present invention are also described by reference to Acoustic Radiation Force Imaging (ARFI) which is described in greater detail, for example, in U.S. Pat. No. 6,371,912, the entire disclosure of which is incorporated herein by reference. An acoustic radiation force may be used to apply a force to tissue thereby causing the tissue to move in the direction of the force and/or to generate a shear wave.

As used herein, a "shear wave" is a form of sample displacement in which a shear wave source, such as ultrasound energy, is transmitted into the sample in one direction and generates an extended shear wave the propagates in another direction that is substantially orthogonal to the direction of the shear wave source. The displacement caused by a shear wave source may be in a range between about 0.1 µm and about 300 µm. Other displacements can be provided.

The term "time of arrival" refers herein to the measured elapsed time between the transmission of a transmitting signal and the return of a corresponding reflected signal. The time of arrival is measured by conventional measurement techniques.

As illustrated in FIG. 1, an ultrasound system 10 includes a controller 20, a signal analyzer 30 and an ultrasound transducer array 40. The ultrasound transducer array 40 may include a plurality of array elements 42 at positions $P_1$ through $P_N$. The array elements 42 are configured to transmit and receive ultrasound signals 50, and may be contacted to a target medium such as a tissue medium 60. As illustrated, the tissue medium, 60 includes a target region 62, which can include a portion or all of the tissue medium 60. The ultrasound array 40 may include ultrasound array elements 42 that define transmit/receive locations for transmitting and receiving ultrasound signals along a direction D1. In some embodiments, the array 40 may be configured to transmit sufficient ultrasound energy, for example, by applying an impulse excitation acoustic radiation force to the medium 60, to generate a shear wave that propagates in a direction D2 that is orthogonal to D1. The array 40 may also be configured to interrogate the tissue medium 60, for example, using ARFI or B-mode imaging techniques to monitor the tissue through time before and/or after the shear wave excitation force has been applied. ARFI imaging is discussed in U.S. Pat. Nos. 6,371,912; 6,951,544 and 6,764,448, the disclosures of which are hereby incorporated by reference in their entireties. Shear waves are discussed in U.S. Pat. Nos. 8,118,744 and 6,764,448, the disclosures of which are hereby incorporated by reference in their entireties. The ultrasound transducer array 40 may be a one-dimensional array configured to generate two-dimensional images or the ultrasound transducer array 40 may be a two-dimensional array configured to generate three-dimensional images.

The controller 20 may include a shear wave generation module 22 and the signal analyzer 30 may include statistical inference analyzing module 32. The shear wave generation module 22 and the statistical inference analyzing module 32 may be configured to control the array 40 and/or to analyze echo signals received by the array 40 as described herein. The shear wave generation module 22 and the statistical inference analyzing module 32 may include hardware, such as control and/or analyzing circuits, and/or software stored on a non-transient computer readable medium for carrying out operations described herein.

Figure 2:
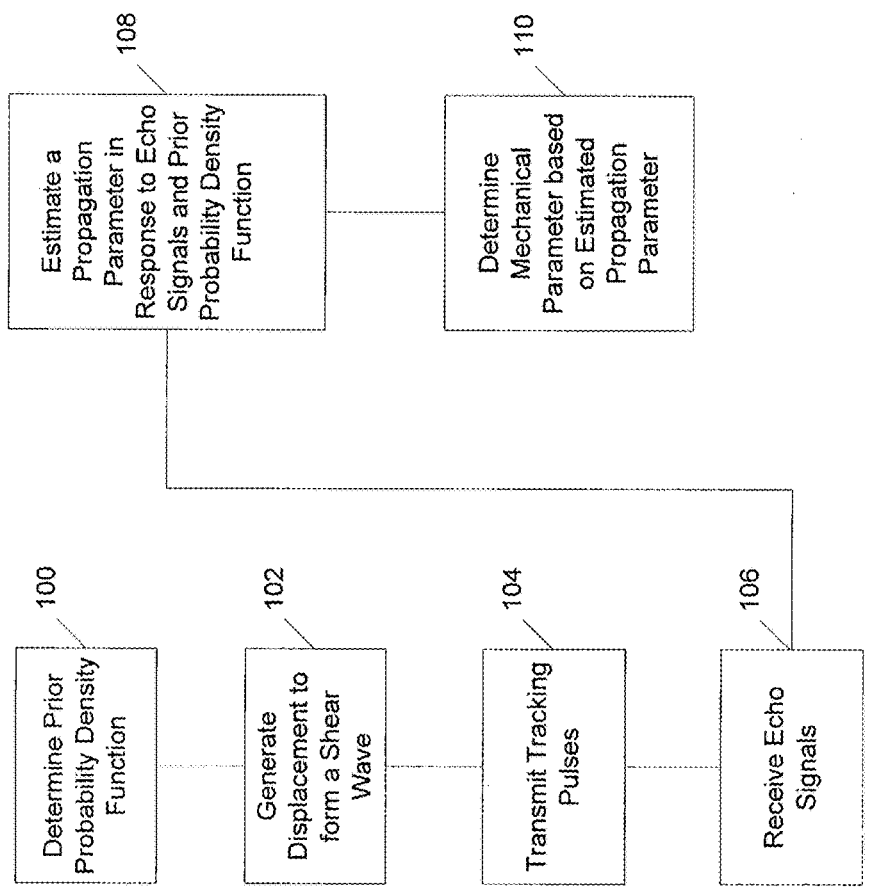
FIG. 2 is a flowchart illustrating operations according to some embodiments.

As illustrated in FIGS. 1 and 2, the statistical inference analyzing module 32 may determine a prior probability density function that characterizes at least one physical property of the target region (Block 100). The shear wave generation module 22 may provide control signals to cause the array 40 to generate a shear wave in the target region 62 (Block 102), to transmit tracking pulses in the target region 62 (Block 104) and to receive corresponding echo signals for the tracking pulses in the target region 62 at a plurality of positions (Block 106). The statistical inference analyzing module 32 estimates a propagation parameter of the shear wave in response to the echo signals and the prior probability density function using statistical inference (Block 108) and determines at least one mechanical parameter of the target region 62 based on estimated propagation parameter (Block 110). The mechanical parameter may include a shear elasticity modulus, Young's modulus, dynamic shear viscosity, shear wave velocity and/or mechanical impedance of the sample. The signal inference analyzing module 32 may be configured to provide an ultrasound image based on the received ultrasound signals and/or the calculated mechanical parameters.

Estimating a propagation parameter at Block 108 may include estimating a likelihood function based on the echo signals, for example, according to Bayesian probability techniques. For example, a maximum a posteriori estimator (MAPE) may be used. The prior probability density function may include data that characterizes one or more physical properties of the target region, such as acoustic radiation force impulse (ARFI) displacement magnitude, B-mode brightness and/or shear wave image data. In some embodiments, the prior probability density function may include noise values for image data (ARFI, B-mode or shear wave images), and the prior probability density function may identify boundary conditions based on noise values such that a change in signal-to-noise ratios indicates the presence of a boundary condition (e.g., a change in stiffness) in the sample. For example, in B-mode imaging, a higher signal-to-noise ratio may indicate a boundary condition such as a change in stiffness in the sample, and in shear wave imaging, a lower signal-to-noise ratio may indicate a boundary condition such as a change in stiffness in the sample.

The likelihood function may be a function that describes the wave arrival time estimates and may be based on a wave arrival time estimator (e.g., a conventional shear wave arrival time estimator using linear regression analysis to estimate shear wave arrival times). The likelihood function may include a shear wave arrival time estimate that is based on the echo signals, such as a shear wave arrival time estimate that is based on a cross-correlation, a time-to-peak displacement, and/or a time-to-peak slope. The statistical inference may include a Bayesian probability based on the likelihood function and the prior probability density function. Accordingly, for a maximum likelihood estimator (MLE) estimate that does not use statistical inference, the shear wave arrival time estimates for the likelihood function are assumed to be Gaussian distributed, and the maximum likelihood estimator (MLE) estimate is a least squares linear regression of the wave arrival time versus lateral position. In contrast, statistical inference may use the same likelihood function combined with a prior probability density function, such as a generalized Gaussian prior distribution. In some embodiments, the statistical inference shear wave speed estimator reduces the variance and/or bias of the shear wave speed estimates, which may reduce noise and allow for smaller regression kernels to be utilized to potentially improve the spatial resolution of the images.

In some embodiments, the shear wave and/or displacement data acquired as described herein can be used to quantify the stiffness of tissues and/or organs, which may be useful in the clinical setting to track the progression of disease and to monitor the response of diseased tissues to treatments (e.g., drug regimens, diet/lifestyle changes, chemotherapy, and radiotherapy). The techniques described herein can be used to characterize the stiffness of biological tissues using their dynamic displacement response to impulsive acoustic radiation force excitations. This may allow for absolute and relative quantification of tissue stiffness to aid in clinical treatment of a variety of pathologic conditions, such as liver disease (e.g., liver steatosis, liver fibrosis and cirrhosis), atherosclerosis, benign prostatic hyperplasia (BPH), muscular dystrophy, products of ablation, cancer in various organs/tissue, thyroid disease and/or skin diseases. Accordingly, the tissue sample may be an in vivo human tissue sample. The shear waves can be detected and/or generated using an internally inserted ultrasound probe array (such as an ultrasound probe array configured for insertion into an orifice of the body) or with an externally applied ultrasound array.

The mechanical parameter(s) of the sample can be correlated to measurement of healthy/diseased tissue states, such as by using actual clinical data and known healthy/diseased tissue states. The clinical data can be based on other factors such as demographic information, e.g., age, gender and race, to correlate the measurement of the mechanical parameter(s) with a measurement of healthy/diseased tissue states in a particular demographic group.

In some embodiments, the mechanical parameter(s) of the sample can be monitored as a function of time by performing the shear wave analyzing techniques described herein on a sample repeatedly over a period of time. A healthy/diseased tissue state determination can be based on a change in the mechanical parameter(s) as a function of time. For example, the mechanical parameter(s) can be monitored over a period of minutes, hours, days, weeks, months or even years to determine the progression of the disease and/or the efficacy of treatment.

In some embodiments, the mechanical parameter(s) may be used to form an ultrasound image, such as a B-mode image or an ARFI image.

Embodiments according to the invention will now be described with respect to the following non-limiting examples.

Time-of-Flight Estimation

The following exemplary techniques may be used to reduce noise in shear wave estimation by recasting the estimation problem as a Bayesian problem to also include prior information about the expected local smoothness of the reconstructed shear wave speed images.

The development of a maximum a posteriori estimator (MAPE) may be based on the traditional time-of-flight based algorithms by considering linear regression, which is a maximum likelihood estimator (MLE) for shear wave speed. To relate the shear wave speed to the wave arrival times, the tissue within the reconstruction kernel is assumed to be homogeneous and isotropic such that the wave arrival times are linearly related to the shear wave speed. This relationship is given by:

$$T_k = \left(\frac{x_k}{S} + b\right), \quad (2)$$

where $T_k$ is the measured wave arrival time at position $x_k$ with shear wave speed S, and y-intercept b, which is the amount of time required for the shear wave to start propagating away from the region of excitation.

However, equation 2 does not account for any noise in the system. Assuming the wave arrival time estimates are Gaussian distributed and considering all of the data within the reconstruction kernel K, the probability that the set of wave arrival times (T=(T_k|k∈K)) was measured given the shear wave speed (S) and intercept (b) is the product of a set of exponential functions, known as the likelihood function:

$$P(T|S) = \prod_{k \in K} \exp\left(-\frac{\left(T_k - \left(\frac{x_k}{S} + b\right)\right)^2}{2\sigma^2}\right) \quad (3)$$

The MLE estimate of the shear wave speed is the value for which equation 3 is maximized. By taking the logarithm of both sides, a more tractable version of the equation is obtained:

$$\log(P(T|S)) = \prod_{k \in K} \exp\left(-\frac{\left(T_k - \left(\frac{x_k}{S} + b\right)\right)^2}{2\sigma^2}\right) \quad (4)$$

which is known as the log-likelihood function.

Both b and S can be solved for by taking the respective derivatives and setting the equations equal to zero. The resulting solution for the MLE estimate, $\hat{S}$, is equation 5, which is the least squares linear regression.

$$\hat{S} = \frac{\sum_{k \in K} (\tilde{x}_k^2)}{\sum_{k \in K} (\tilde{T}_k \tilde{x}_k)} \quad (5)$$

$$\tilde{T}_k = T_k - \frac{1}{k} \sum_{k \in K} T_k$$

$$\tilde{x}_k = x_k - \frac{1}{k} \sum_{k \in K} x_k$$

To obtain a SWEI image, the MLE must take into account the data at each pixel, which mathematically yields the combined probability in equation 6. In this equation, the subscript i indicates the value at a given pixel in the image. The shear wave speed ($S_i$), y-intercept ($b_i$) and reconstruction kernel ($K_i$) are all a function of the pixel number, but the positions ($x_k$) and associated wave arrival time data ($T_k$) are not. The likelihood function for the entire image (equation 6) is the product of the likelihood functions for each individual pixel (equation 3). Again considering the log-likelihood function, equation 7 must now be maximized to determine the MLE estimate for the SWEI image.

$$P(T|S) = \prod_i P(T|S_i) \quad (6)$$

$$\log(P(T|S)) = \sum_i \log(P(T|S_i)) = \sum_i \left(\sum_{k \in K_i} \exp\left(-\frac{\left(T_k - \left(\frac{x_k}{S_i} + b\right)\right)^2}{2\sigma_i^2}\right)\right) \quad (7)$$

Since equation 7 is a summation and each term is independent, they can be maximized individually. Therefore, the resulting solution for the MLE estimate at a given pixel ($\hat{S}_i$) is still equation 5.

Maximum a Posteriori Estimate of SWS Images

The least squares linear regression log-likelihood function (equation 7) may be used to develop a maximum a posteriori estimator (MAPE) by combining it with a prior probability, P (S), for the image. In this formulation, equation 8 gives the log-likelihood function that must be optimized, with an arbitrary prior distribution.

$$\log(P(T\mid S)P(S)) = \sum_i (\log P(T\mid S_i) + \log P(S_i)) \quad (8)$$

One prior distribution that can be used is an exponential function:

$$\log(P(S_i)) = \sum_{j \in N_i} \left( \frac{-a_{ij}}{\lambda} \left| \frac{1}{S_i} - \frac{1}{S_j} \right| \right), \quad (9)$$

where aij is the weight of pixels in the neighborhood $N_i$ and $\lambda$ characterizes the width of the exponential function. This prior distribution introduces a penalty term when the shear wave speed within a neighborhood is not uniform. The MAPE estimate, $\hat{S}_{MAPE}$, is the maximum value over the domain S after substituting the likelihood function and prior distribution into equation 8, resulting in equation 10. Since the terms in the summation are not independent, an optimization algorithm must be utilized such as conjugate gradient descent or iterative coordinate descent.

$$\hat{S}_{MAPE} = \underset{S}{\mathrm{argmax}} \sum_i \left( \sum_{k \in K_i} \left( -\frac{\left(T_k\left(\frac{x_k}{S_i} + b_i\right)\right)^2}{2\sigma_i^2} \right) + \sum_{j \in N_i} \left( \frac{-a_{ij}}{p\lambda^p} \left| \frac{1}{S_i} - \frac{1}{S_j} \right|^p \right) \right) \quad (10)$$

Finite Element Method (FEM) Simulations

Previously validated finite element method (FEM) simulations were adapted to analyze the performance of the MAPE for shear wave speed estimation. See M. L. Palmeri, S. Member, A. C. Sharma, R. R. Bouchard, R. W. Nightingale, and K. R. Nightingale, "A Finite-Element Method Model of Soft Tissue Force," IEEE transactions on ultrasonics, ferroelectrics, and frequency control, vol. 52, no. 10, pp. 1699-1712, 2005; M. L. Palmeri, S. A. McAleavey, G. E. Trahey, and K. R. Nightingale, "Ultrasonic tracking of acoustic radiation force-induced displacements in homogeneous media." IEEE transactions on ultrasonics, ferroelectrics, and frequency control, vol. 53, no. 7, pp. 1300-1313, July 2006. [Online]. Available: http://www.pubmedcentral.nih.gov/articlerender.fcgi?artid=1815396&tool=pmcentrez&rendertype=abstract. A three-dimensional, rectangular, solid mesh was created for the FEM simulations with dimensions of 18 mm laterally (x), 10 mm in elevation (y), and 40 mm axially (z) using LS-PREPOST2 (Livermore Software Technology Corp., Livermore, Calif.), such that each element was cubic with a side length of 0.2 mm. The boundary conditions of the mesh were defined to have quarter-symmetry about the lateral and elevation faces of the mesh (x-z plane, y=0 mm and y-z plane, x=0 mm) and non-reflecting boundary conditions on the back faces (x-z plane, y=10 mm and y-z plane, x=18 mm). Full constraints were assumed for the top and bottom of the mesh (x-y plane, z=0 mm and x-y plane, z=40 mm).

The FEM mesh was defined to simulate stiff spherical lesions ranging from 4 mm to 8 mm in diameter, such that the center of the lesion was located 9 mm laterally from the mesh boundary (x=9 mm, y=0 mm, z=20 mm). The background tissue was modeled as a homogeneous material with a Young's modulus of 7.2 kPa. Each size lesion was simulated to be 2×, 3×, 4×, 6×, and 8× stiffer than the background.

Field II was used to simulate a linear array transducer with a F/2.5, 4.6 MHz, 65 µs pushing pulse focused at 20 mm (x=0 mm, y=0 mm, z=20 mm). After obtaining the three-dimensional acoustic intensity profile, the force was computed at each node in the mesh, scaled by the uniform element volume. The pushing pulse was simulated such that as the shear wave propagated away from the region of excitation it would pass through the spherical lesion.

The FEM simulations were performed using an explicit time-domain finite element algorithm available in LS-DYNA (Livermore Software Technology Corp., Livermore, Calif.); the total time simulated was 12 ms, and nodal displacement data were saved every 0.1 ms, corresponding to a 10 kHz sampling rate. Ultrasonic tracking was then simulated using Field II and the displacement data output from the FEM simulation; the same linear array transducer definition was used, but with a F/2 focal geometry, 7 MHz, 1-cycle excitation, with F/0.5 dynamic receive and receive aperture growth. The output of the Field II simulation was a set of radio-frequency (RF) A-lines, and normalized cross-correlation was used to estimate the tissue displacement with a kernel length and search region of 1.5× and 0.4× the acoustic wavelength, respectively. For each FEM simulation, ten speckle realizations were simulated using Field II.

Figure 3:
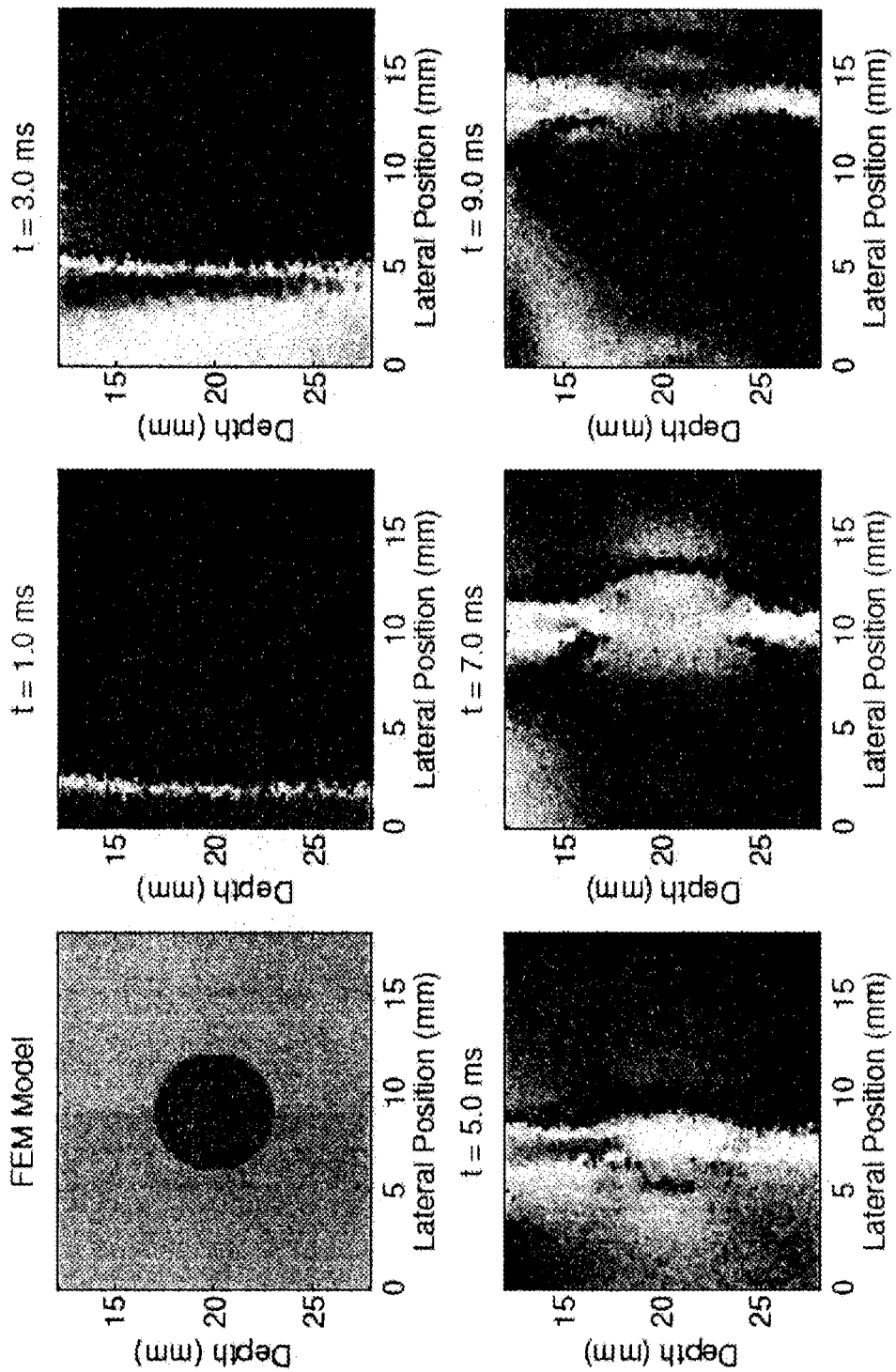
FIG. 3 illustrates digital images using an example finite element method (FEM) simulation mesh of a 6 mm, 28.8 kPa Young's modulus lesion (top left) and ultrasounically tracked displacement at 5 time points after the simulated radiation force excitations in which the displacements are on a decibel scale of [−20, 20] db according to some embodiments.

An example of the simulated, ultrasonically tracked shear wave propagation through the 6 mm, 28.8 kPa Young's modulus lesion is given in FIG. 3. The shear wave propagates left to right. Observing the shear wave 1.0 and 3.0 ms after the radiation force excitation, the wavefront is nearly vertical since the background tissue is homogeneous. Once the shear wave enters the stiffer lesion, part of the shear wave energy is reflected at the boundary, and the wavefront bends to accommodate the faster speed inside the lesion, as seen in the 5.0 ms figure. As the shear wave exits the lesion, additional energy is again reflected, and on the far side of the lesion at 9.0 ms, two shear wavefronts can be observed, one corresponding to the wave that propagated through the lesion, the other to the wave that propagated around the lesion only in the background material.

Wave Arrival Time Estimation

After displacement estimation, multiple data processing steps were applied to obtain the estimates for the wave arrival time. First, a correlation coefficient filter was applied to remove data with correlation coefficients below 0.995; the removed data points were then interpolated from the surrounding data. Next, a 0.75 mm axial median filter was applied, then the data were differentiated to determine the tissue velocity, and a second-order low-pass Butterworth filter with a 1000 Hz cutoff frequency was applied to remove high frequency jitter from the velocity data at each pixel. The data were then downsampled spatially to 0.1×0.2 mm axial by lateral, and upsampled temporally to a sample rate of 50 kHz. Finally, a directional filter was applied to each axial plane individually to isolate the right propagating shear waves.

The wave arrival time ($T_k$) for each lateral position ($x_k$) was determined at each depth individually by first estimating the incremental wave arrival time between adjacent lateral positions, and then calculating the cumulative sum of the incremental arrival times to determine the absolute wave arrival time. For adjacent lateral positions, the incremental arrival time ($T_{k+1}-T_k$) was estimated by performing cross-correlation between the upsampled velocity vs. time waveforms for each pair of adjacent lateral locations. After the maximum correlation was found, a parabolic sub-sample estimator was used to obtain the final estimate of the wave arrival time. The cumulative sum of the incremental wave arrival times were then used to estimate the shear wave speed at each spatial location.

Figure 4:
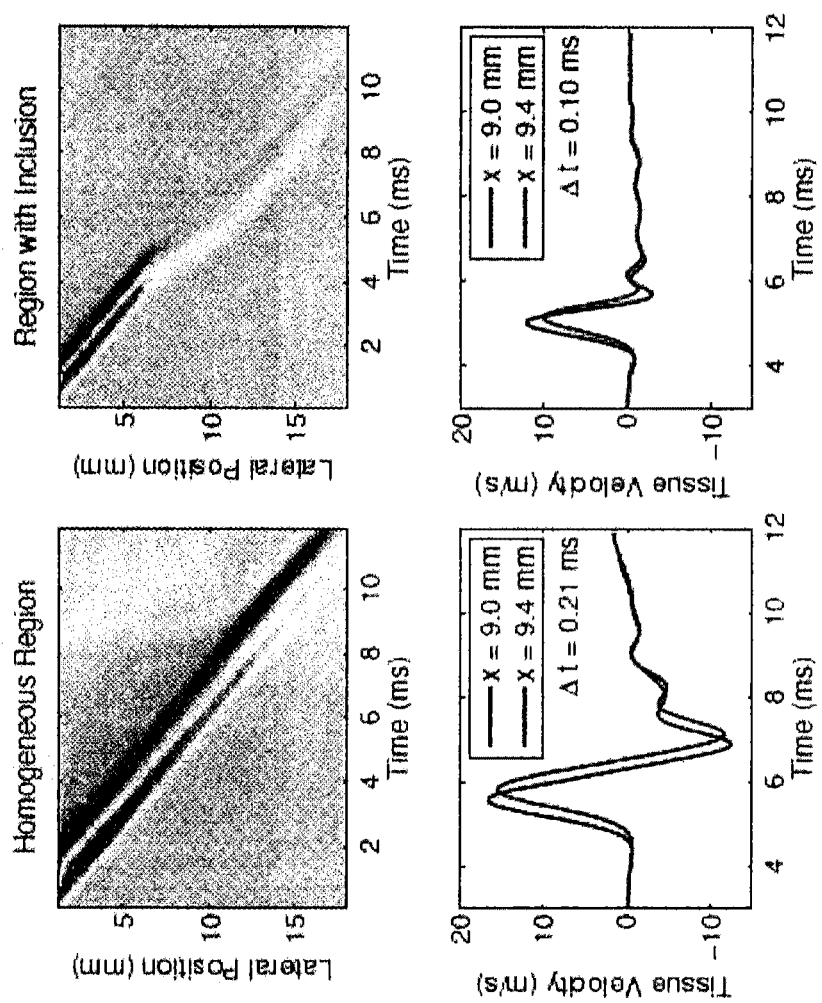
FIG. 4 illustrates images of the the tissue velocity after ultrasonic tracking, preprocessing and directional filtering as a function of lateral position and time for a homogeneous region (top left) and a region with a 6 mm, 28.9 kPa inclusion (top right), and corresponding graphs of the tissue velocity versus time (bottom left, bottom right) that demonstrate the computation of the incremental wave arrival time between adjacent lateral locations using cross-correlation and a parabolic sub-sample estimator according to some embodiments.

The example data set from FIG. 3 was plotted as a function of time and lateral position for a homogeneous region (13 mm axially) and a region with the simulated 6 mm, 28.8 kPa inclusion (20 mm axially) in the two top images in FIG. 4. The homogeneous region (FIG. 4, top left) has a smooth wavefront as the shear wave propagates across all of the lateral positions. The difference in shear wave speed in the region with the inclusion is clearly visible as the wavefront propagates through a larger lateral region in the same amount of time (FIG. 4, top right); additionally, a secondary wavefront on the far side of the lesion is also visible here.

The bottom plots of FIG. 4 show the cross-correlation method for computing the incremental wave arrival time between successive lateral positions. In each of these plots, the cross-correlation between the velocity versus time waveforms was obtained, and after using the parabolic sub-sample estimator, a AT value was computed corresponding to the time for the shear wave to propagate from one lateral position to the next.

Figure 5:
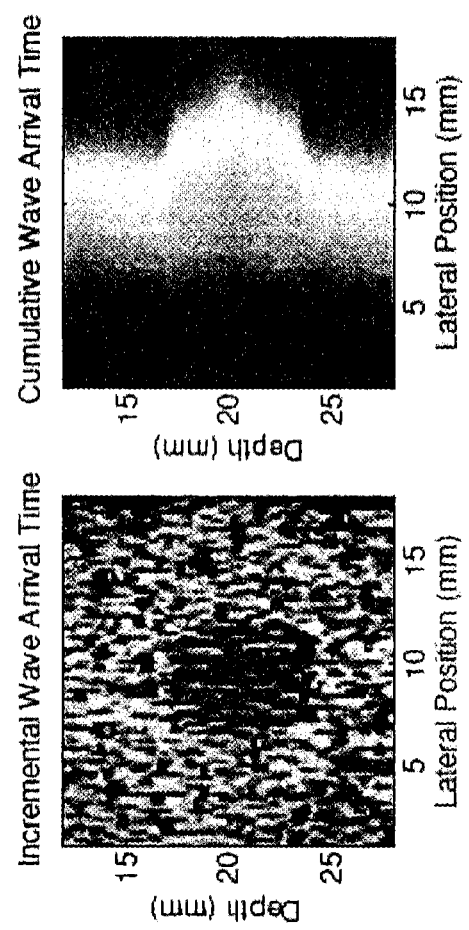
FIG. 5 illustrates images of the incremental (left image) and cumulative (right image) wave arrival times, which are shown as a function of lateral and axial images according to some embodiments.

The incremental wave arrival time for each pixel in the image was obtained and is shown in the left image of FIG. 5. Although this image is very noisy, the lesion is still visible, however, to obtain robust estimates of the shear wave speed, linear regression is typically performed as a function of lateral positions using the cumulative wave arrival time data (right image, FIG. 5), with the slope of the regression corresponding to the estimated shear wave speed.

Shear Wave Speed Estimation

Time-of-flight algorithms typically perform a least squares linear regression of the wave arrival time data versus lateral position to estimate the shear wave speed. In contrast, the proposed adaptive filter utilizes the posterior distribution comprised of the likelihood function from least squares linear regression, combined with an exponential prior distribution as discussed herein. The prior distribution provides a spatial continuity constraint for the image by comparing the shear wave speed at each pixel with the surrounding pixels in a given neighborhood using a previously determined model for the expected amount of noise in the linear regression estimates.

For each simulated speckle realization of the FEM simulations, the least squares linear regression shear wave speed image was computed using regression kernel lengths ranging from 1.0 mm to 4.0 mm laterally. Additionally, a noise image was computed, where each pixel corresponds to the standard deviation of the residuals for each regression kernel:

$$\sigma_i = \sqrt{\frac{1}{N}\sum_{k \in K_i}\left(T_k - \frac{x_k}{S_i}\right)^2}, \quad (11)$$

where N is the number of points used in the regression.

Using the least squares linear regression shear wave speed image and the noise image, the constrained nonlinear optimization of equation 10 was performed using the fmincon function in MATLAB (The MathWorks Inc., Natick. Mass.), where the image data were used as the initial guess and the values of $\sigma_i$ in equation 10 correspond to the values computed using equation 11. Constrained optimization was chosen to limit the possible range of shear wave speed values to appropriate estimates (i.e., negative speeds were not permitted and maximum speed of 8 m/s was considered).

Each pixel in the neighborhood region of the prior distribution was given equal weighting (i.e., $a_{ij}=1$ in equation 10). By choosing this specific prior distribution, the analytic gradient vector and Hessian matrix were computed, allowing for more rapid optimization using finincon. The neighborhood region was selected as a circular region around the pixel, with the radius varying from 1.0 mm to 4.0 mm in size. Additionally, the width of the prior distribution was varied such that λ ranged from $10^4$ to $10^3$ m/s. In total, seven regression kernel sizes, seven neighborhood sizes. and twenty-five values of λ were analyzed for each speckle realization.

Image Analysis

For each of the least squares linear regression and MAP estimated shear wave speed images, the root mean squared (RMS) error was computed. Since the exact size, stiffness, and position of the lesion are known from the FEM simulation, the true shear wave speed was subtracted from the estimated SWS image and the RMS error for the image was computed as the mean RMS error over a region twice the area of the lesion.

To analyze lesion conspicuity, both the contrast and the contrast to noise ratio (CNR) of the lesions were computed. The contrast was computed as $S_{in}/S_{out}$, where $S_{in}$ is the mean shear wave speed inside the target and $S_{out}$ is the mean shear wave speed outside the target. The contrast to noise ratio (CNR), which is generally considered a better metric for lesion conspicuity, was computed in the same region of interest as $(S_{in}-S_{out})/\sqrt{\sigma_{in}^2+\sigma_{out}^2}$ where $\sigma_{in}$ and $\sigma_{out}$ are the standard deviation of the shear wave speed inside the target and outside the target, respectively. Analyses are performed with comparisons between the different sizes and stiffness of the FEM simulations and reconstruction parameters, with error bars computed over the 10 speckle realizations used for each simulation.

Results

Figure 6:
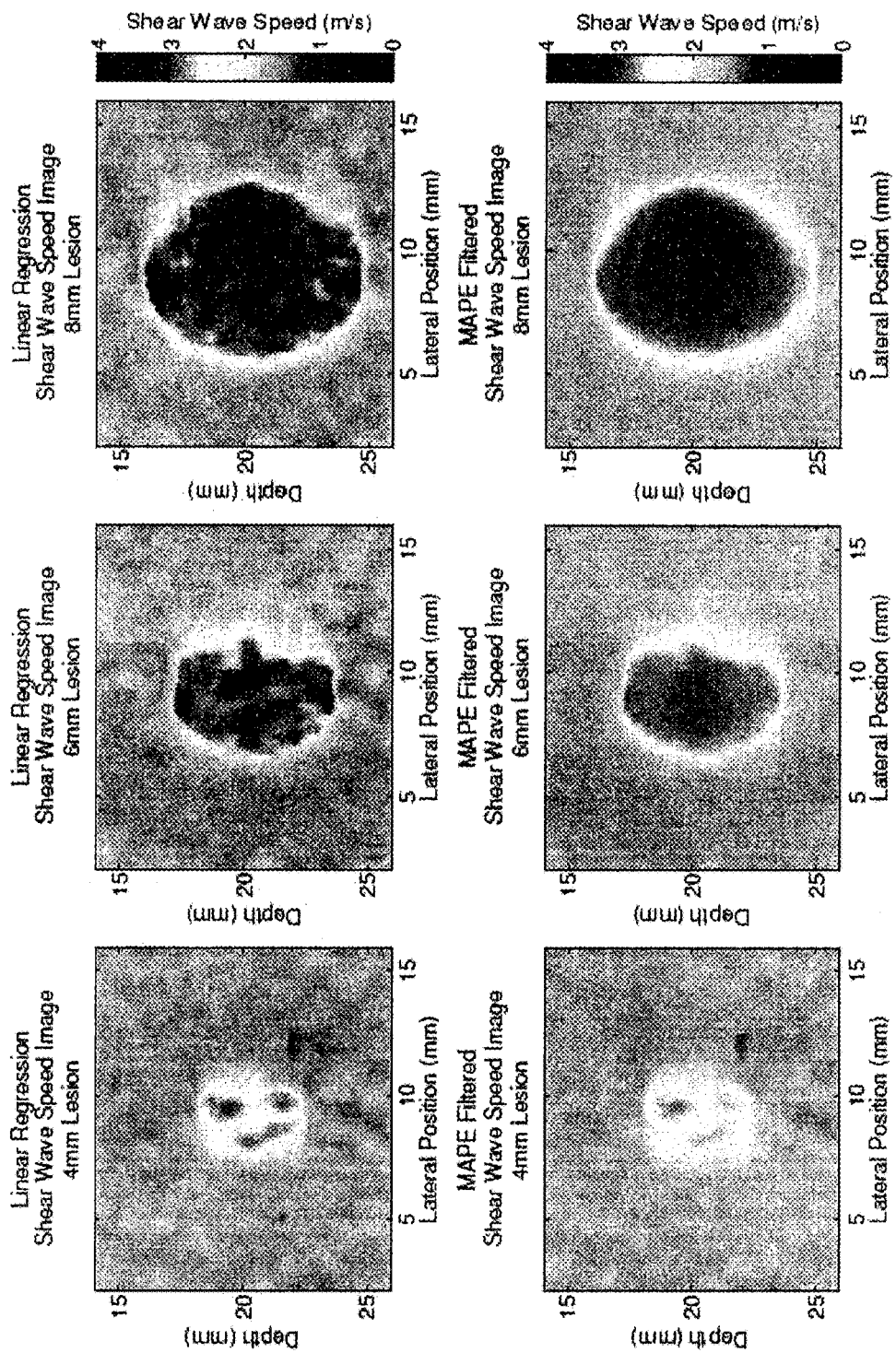
FIG. 6 illustrates example linear regression and MAPE filtered shear wave speed images of a 28.8 kPa Young's modulus inclusion using a 1.5 mm linear regression kernel. A small regression kernel with linear regression is shown in the top row, and shear wave image speeds after applying the MAPE filter are shown in the bottom row according to some embodiments.
Figure 7:
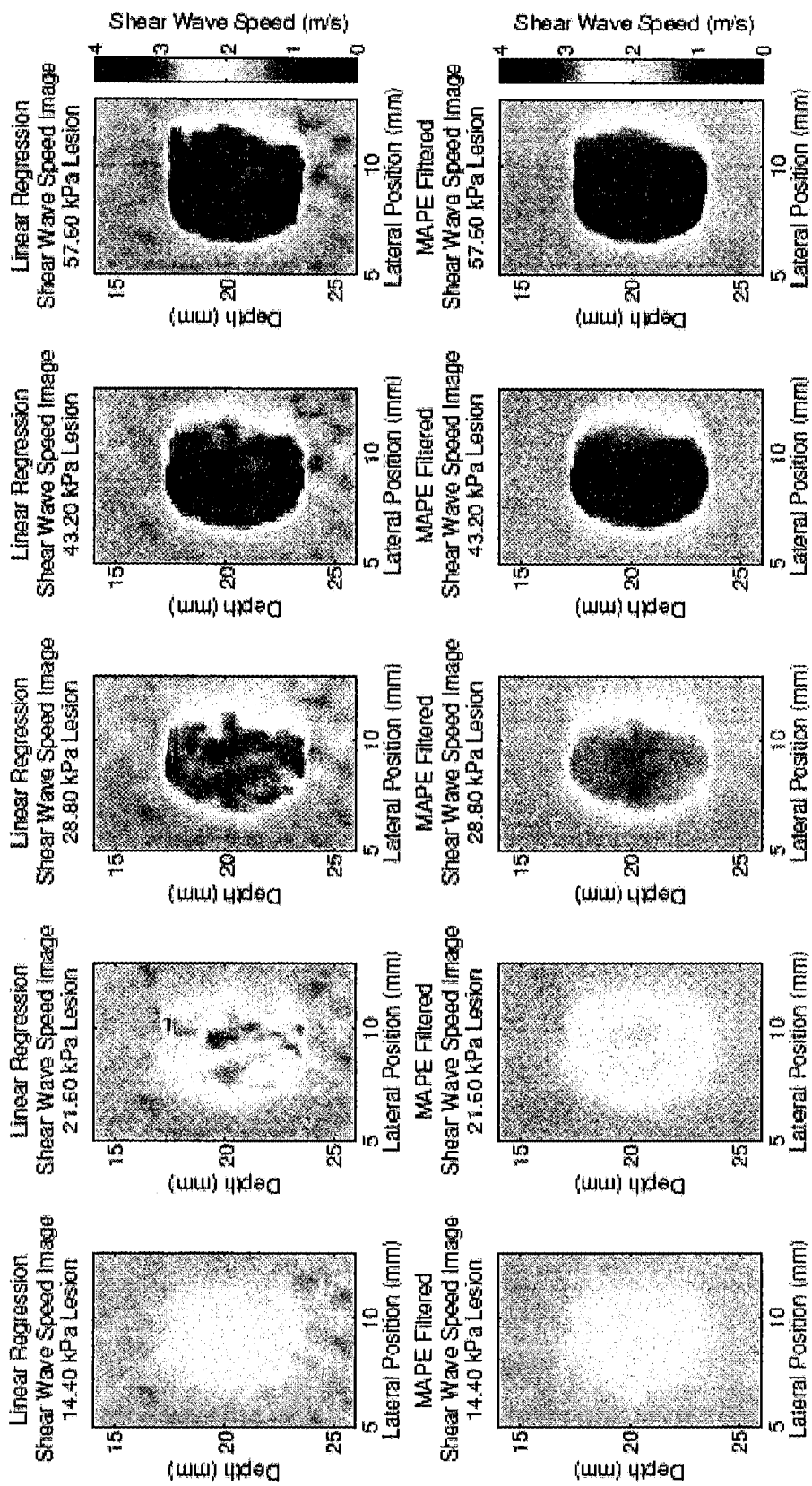
FIG. 7 illustrates example linear regression and MAPE filtered shear wave speed images of 6 mm diameter inclusions for a range of stiffnesses using a 1.5 mm linear regression kernel for various Young's moduli according to some embodiments.

For each size and stiffness combination, shear wave speed images were generated and examples of the variations of the images with size and stiffness are given in FIGS. 6 and 7, respectively. In FIGS. 6 and 7, a 1.5 mm linear regression kernel was used and the top row of images depicts the result for least squares linear regression on the cumulative wave arrival time data shown in FIG. 5. Utilizing the linear regression images as the initial guess and the estimate for $\sigma_i$ given by equation 11, the nonlinear constrained optimization of equation 10 was performed and resulted in the bottom row of images, the MAPE filtered images.

To analyze the impact of the MAPE filter on the shear wave speed images, the RMS shear wave speed error was computed, given in units of m/s. This error was computed as a function of regression kernel and neighborhood size (from equation 9) in FIGS. 8 and 9 for the 6 mm, 28.8 kPa Young's modulus lesion. Since the regression kernel length is fixed in FIG. 8, the computed error of the least squares linear regression image is given as the dashed line, which is a fixed value as a function of λ, the width of the exponential prior distribution. However, depending on the neighborhood size and the value of λ, the overall error in the image could be greater or less than the nominal error from the linear regression estimate. Comparing the individual plots of FIG.

9, the optimal value of λ is most dependent on the neighborhood size, not the regression kernel size.

Figure 10:
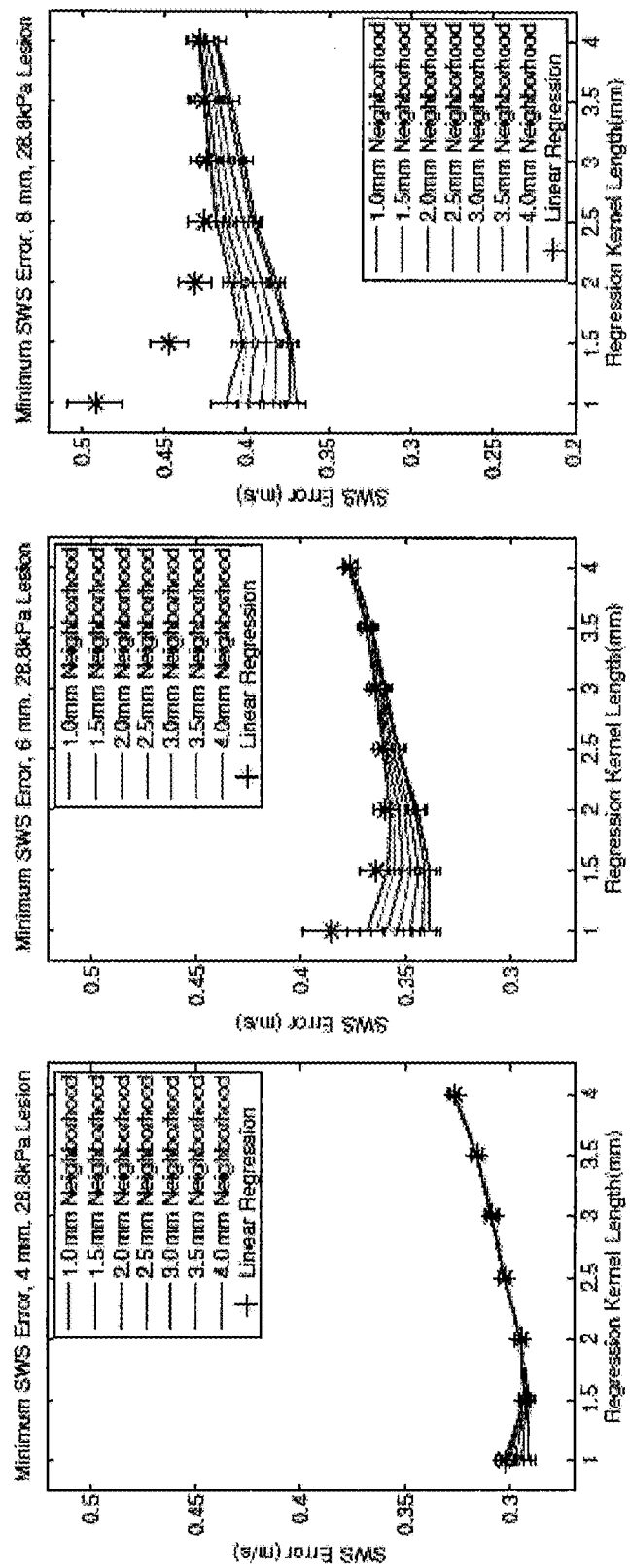
FIG. 10 illustrates graphs of shear wave speed error as a function of regression kernel length and neighborhood size evaluated using an optimal value of $\lambda$ for 4 mm (left), 6 mm (center) and 8 mm (right) lesions according to some embodiments.

By taking the minimum error as a function of 2 for each set of linear regression kernel, neighborhood size, and simulation, the data in FIG. 10 is obtained. The error bars indicate the standard deviation of the shear wave speed error over the 10 speckle realizations that were simulated. Overall, for the 4 mm lesion (FIG. 10, left plot), there is little difference between the error achieved when using the MAPE filtered images as compared to the linear regression images; however, for the larger lesions, significant error reductions were achieved, such as the 25% shown for the 28.8 kPa lesion and over 40% for the 43.2 kPa and 57.6 kPa lesions (not shown).

Figure 11:
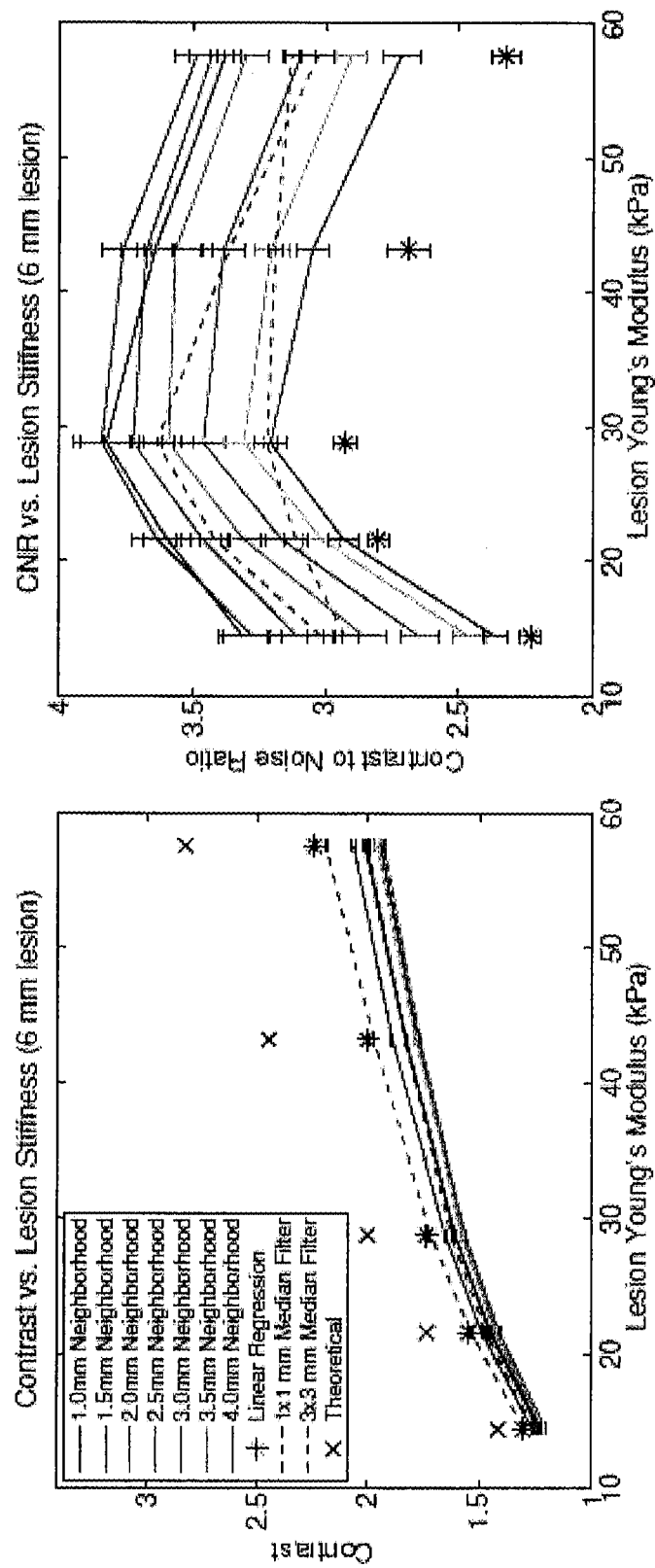
FIG. 11 illustrates graphs of the contrast (left) and CNR (right) values, with the standard error for each, as a function of the lesion stiffness and neighborhood size for the 6 mm diameter lesion using the 1 mm linear regression kernel according to some embodiments.

Although the computation of the total error in the shear wave speed image gives an indication of the accuracy of the shear wave speed image as compared to the true shear velocity, it does not indicate lesion conspicuity. For this purpose, the contrast and CNR were computed and are given in FIG. 11 for the 6 mm diameter lesion using the 1 mm linear regression kernel. In these plots, a single value of λ was chosen based only on the neighborhood size, as the results from FIG. 9 indicated that was the most impactful parameter in choosing λ. Additionally, the contrast and CNR results were also compared to using a 2D median filter. As expected, FIG. 11 demonstrates that the use of the MAPE filter reduces the image contrast, which is due to the filter increasing bias, but it also significantly increases the CNR, by as much as 50%, since the filter is designed to reduce the noise.

Discussion

As the popularity and utility of shear wave elasticity imaging has increased, so has the complexity of the targets it is being used to image. When imaging these more complex targets, smaller regression kernels may be used to achieve the desired resolution, however the increased noise confounds image interpretation. As described herein, a formulation of a maximum a posteriori (MAP) estimator is used as an adaptive filter for shear wave speed images, which yielded a reduction in the error as well as an increase in the CNR of the targets.

Demonstrated in FIGS. 6 and 7, the MAPE filter is able to utilize the linear regression estimates and the noise image in order to improve the overall image quality, independent of size or stiffness of the target being imaged. Because the MAPE filter uses independent noise estimates at each pixel, it retains high quality shear wave speed estimates, while filtering low quality estimates based upon surrounding data. Additionally, by utilizing the exponential function, it is able to retain sharp edges.

The denoising effects of the MAPE filter are present in all of the examples given in FIGS. 6 and 7; however, those images were generated using the optimal value for the width of the exponential distribution (λ) for a given regression kernel and neighborhood size. As detailed in FIGS. 8-10, the error resulting from the use of the MAPE filter may be dependent on all of these parameters. Specifically, for FIGS. 8 and 9, the interpretation as a function of λ can be based in two main groups. If λ is very small, the exponential prior distribution dominates equation 10 and essentially forces the entire image to have a single value, which has a high error as computed from the bias and variance. Alternatively, if λ is very large, the exponential prior term is very small in equation 10, and the MAPE filtered images are essentially no different than the original least squares linear regression images, which results in them having the same value for the SWS error.

Figure 8:
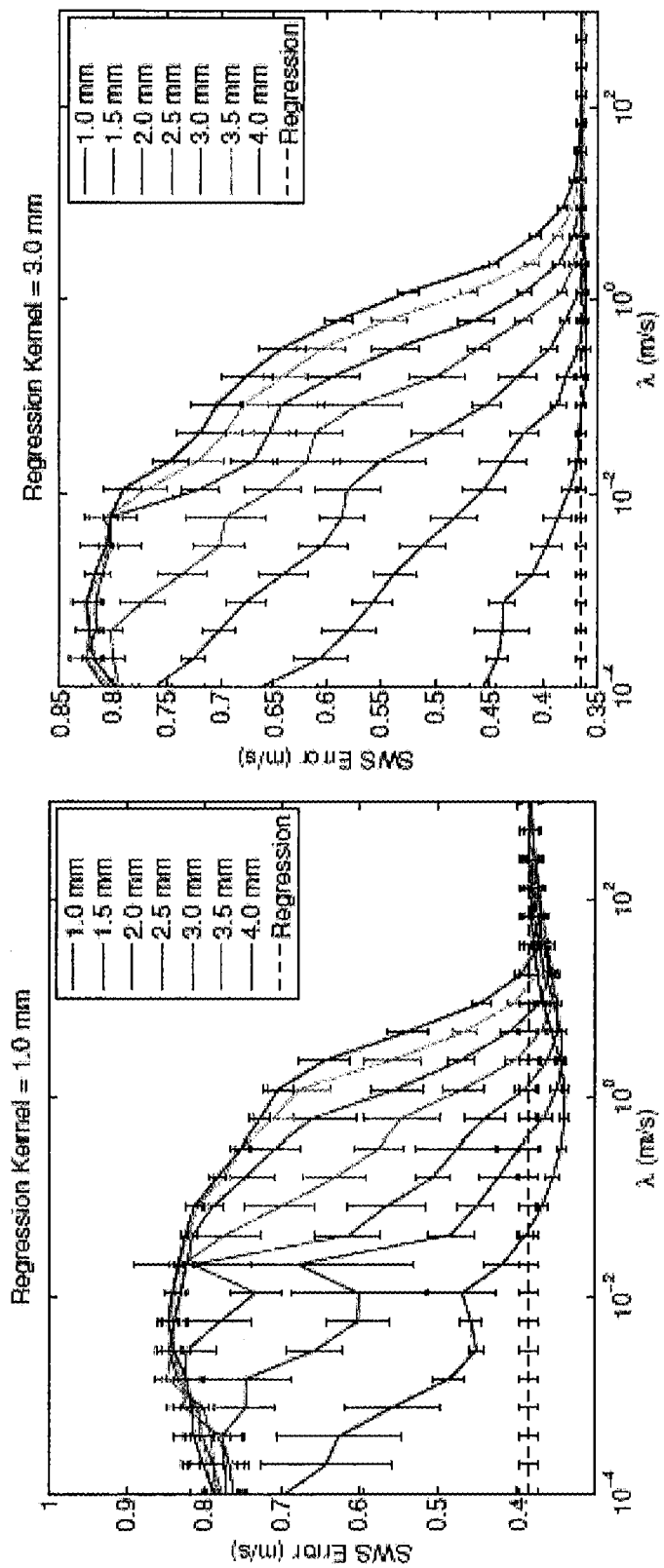
FIG. 8 illustrates graphs of the shear wave speed error in the 6 mm, 28.8 kPa simulation as a function of $\lambda$, the width of the exponential prior distribution, and the size of the neighborhood for a 1.0 mm regression kernel (left) and a 3.0 mm regression kernel (right) according to some embodiments.

Interpreting the figures individually, FIG. 8 details the performance of the adaptive filter for a fixed regression kernel as a function of both the neighborhood size and the width of the prior distribution. For the small regression kernel (FIG. 8, left), the adaptive filter can reduce the overall shear wave speed error below the linear regression estimate, depending on the value of λ; however, for the larger regression kernel (FIG. 8, right), the minimum error is given by the linear regression estimate. The performance of the adaptive filter is therefore highly dependent on the amount of noise originally present in the data (i.e., a large regression kernel has low noise, therefore the filter does not improve image quality, whereas the small regression kernel has high noise, and thus the adaptive filter significantly improves the shear wave speed image).

Figure 9:
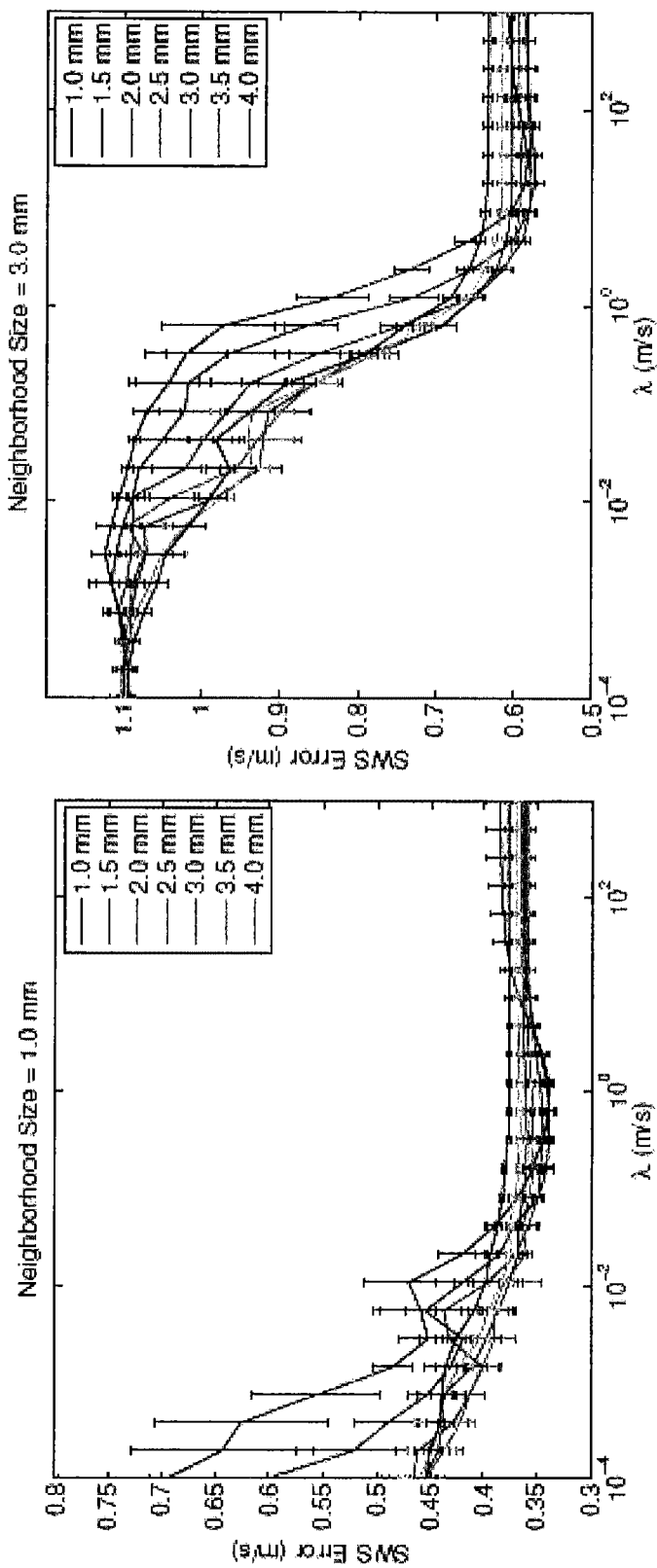
FIG. 9 illustrates graphs of the shear wave speed error for the 6 mm, 28.8 kPa simulation as a function of $\lambda$, the width of the exponential prior distribution, and the regression kernel size for fixed neighborhood sizes of 1.0 mm (left) and 3.0 mm (right) according to some embodiments.

Although the overall performance of the filter depends heavily on the regression kernel size, FIG. 9 demonstrates that the optimal value of λ is most highly dependent on the neighborhood size, which is expected since it scales the summation of the prior distribution. Additionally, FIG. 9 portrays the range of values of λ for which the MAPE filter improves image quality, which is most evident in the 1 mm regression kernel size. Since the error at the maximum value of 2 corresponds to the linear regression estimate, all values of λ for which the error is less than the error at the maximum value of λ correspond to improvements in image quality. As demonstrated using both the 1.0 mm (FIG. 9, left) and 3.0 mm (FIG. 9, right) neighborhood sizes, λ can vary by upwards of an order of magnitude and still reduce the overall error in the shear wave speed images. This large range of useful values of λ demonstrates that this adaptive filter is stable and flexible for a wide variety of imaging scenarios.

However, to determine the peak performance of the adaptive filter, the width of the prior distribution was optimized in FIG. 10, which depicts the maximum possible reduction in the error achievable as a function of regression kernel, neighborhood size, and target size for a fixed target stiffness. FIG. 10 shows quite a bit of variability with all of the parameters, however, in general, the minimum error is achieved with the smallest regression kernel and the smallest neighborhood size. This trend is also consistent across the different stiffnesses simulated, and is an expected result given that the error computed is a function of the image bias and variance. Theoretically, by using the smallest possible regression kernels, the bias is reduced because there are fewer pixels that span both the background and lesion material, but this typically results in higher amounts of noise or variance. The adaptive filter then provides denoising, allowing for the use of the smallest regression kernels without as much variance.

The quoted shear wave speed error takes into account both the bias and variance, and is therefore a fair estimate of the error in the image, but it does not take into account lesion conspicuity. Additionally, although error reductions were shown by obtaining the minimum error across all values of λ in FIG. 10, this is not a practical image processing scenario as it requires significant computing power to generate each image (10-30 seconds) depending on the nonlinear optimization algorithm.

Thus, to demonstrate the stability of the adaptive filter and its applicability to a more realistic imaging scenario, the contrast (FIG. 11, left) and CNR (FIG. 11, right) were computed for the 6 mm diameter lesion using the 1 mm linear regression kernel. In these plots, a single value of λ was chosen based only on the neighborhood size, as indicated by the results in FIG. 9. As expected, FIG. 11 demonstrates that the use of the adaptive filter reduces the image contrast, which is due to the filter increasing bias, but it also significantly increases the CNR, by as much as 50%, since the filter is designed to reduce the variance. Additionally, the adaptive filter had higher CNR than applying an equivalently sized 2D median filter, which is a standard image processing technique for SWS images.

Through the development of the adaptive filter, multiple choices were made to demonstrate the utility, but also limited the scope of this analysis. The use of the exponential prior distribution, which is a specific choice of a generalized Gaussian prior distribution, allowed for more rapid computation of the final estimate because analytic functions for the gradient and the Hessian matrix could be computed. However, even with these functions, to perform the optimization requires significant computation power, typically taking 10-30 seconds for a single set of parameters with a 8000 pixel image. Additionally, this study was limited to one implementation of an adaptive filter, and investigation of other prior distributions as well as other optimization techniques may be performed.

Accordingly, statistical inference techniques, such as the MAPE adaptive filter, can improve image quality by reducing the overall error in SWEI images as well as increasing the CNR.

The foregoing is illustrative of the present invention and is not to be construed as limiting thereof. Although a few example embodiments of this invention have been described, those skilled in the art will readily appreciate that many modifications are possible in the example embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method for determining a mechanical parameter for a sample having a target region, the method comprising:
   determining a prior probability density function that characterizes a probability distribution of at least one physical property of the target region, wherein the prior probability density function comprises ultrasound data from acoustic radiation force impulse (ARFI), B-mode or shear wave ultrasound interrogations;
   generating a displacement of the sample to form a shear wave that propagates orthogonal to a direction of the displacement;
   transmitting tracking pulses in the target region;
   receiving corresponding echo signals for the tracking pulses in the target region at a plurality of lateral positions;
   estimating a propagation parameter of the shear wave in response to the echo signals and the prior probability density function using statistical inference to infer the propagation parameter; and
   determining at least one mechanical parameter of the target region based on the estimated propagation parameter.

2. The method of claim 1, wherein the prior probability density function comprises acoustic radiation force impulse (ARFI) displacement magnitude and/or B-mode brightness.

3. The method of claim 1, wherein the prior probability density function comprises shear wave image data.

4. The method of claim 1, wherein estimating a propagation parameter comprises estimating a likelihood function comprising a likelihood of shear wave arrival time estimates based on the echo signals.

5. The method of claim 4, wherein the shear wave arrival time estimate is based on a cross-correlation between displacement or velocity profiles at lateral locations, a time-to-peak displacement, and/or a time-to-peak slope.

6. The method of claim 5, wherein estimating a propagation parameter of the shear wave in response to the echo signals and the prior probability density function using statistical inference comprises applying a Bayesian probability to the likelihood function and the prior probability density function.

7. A computer program product for determining a mechanical parameter for a sample having a target region, the computer program product comprising a non-transient computer readable medium having computer readable program code embodied therein, the computer readable program code comprising:
   computer readable program code configured to determine a prior probability density function that characterizes a probability distribution at least one physical property of the target region, wherein the prior probability density function comprises ultrasound data from acoustic radiation force impulse (ARFI), B-mode or shear wave ultrasound interrogations;
   computer readable program code configured to generate a displacement of the sample to form a shear wave that propagates orthogonal to a direction of the displacement;
   computer readable program code configured to transmit tracking pulses in the target region;
   computer readable program code configured to receive corresponding echo signals for the tracking pulses in the target region at a plurality of lateral positions;
   computer readable program code configured to estimate a propagation parameter of the shear wave in response to the echo signals and the prior probability density function using statistical inference to infer the propagation parameter; and
   computer readable program code configured to determine at least one mechanical parameter of the target region based on the estimated propagation parameter.

8. The computer program product of claim 7, wherein the prior probability density function comprises acoustic radiation force impulse (ARFI) displacement magnitude and/or B-mode brightness.

9. The computer program product of claim 7, wherein the prior probability density function comprises shear wave image data.

10. The computer program product of claim 7, wherein the computer readable program code configured to estimate a propagation parameter comprises computer readable program code configured to estimate a likelihood function comprising a likelihood of shear wave arrival time estimates based on the echo signals.

11. The computer program product of claim 10, wherein the shear wave arrival time estimate is based on a cross-correlation between displacement or velocity profiles at lateral locations, a time-to-peak displacement, and/or a time-to-peak slope.

12. The computer program product of claim 11, wherein estimating a propagation parameter of the shear wave in response to the echo signals and the prior probability density function using statistical inference comprising applying a Bayesian probability to the likelihood function and the prior probability density function.

* * * * *

UNITED STATES PATENT AND TRADEMARK OFFICE
CERTIFICATE OF CORRECTION

PATENT NO. : 10,451,587 B2
APPLICATION NO. : 14/801007
DATED : October 22, 2019
INVENTOR(S) : Rosenzweig et al.

Page 1 of 1

It is certified that error appears in the above-identified patent and that said Letters Patent is hereby corrected as shown below:

In the Specification

Column 2, Line 18: Please correct "$\rho g^2$" to read -- $\rho S^2$ --

Column 10, Line 1: Please correct "(5)" to read -- (S) --

Column 10, Line 18, Formula 4: Please correct "$\Pi$" to read -- $\Sigma$ --

Column 13, Line 24: Please correct "AT" to read -- $\Delta T$ --

Column 13, Line 62: Please correct "Nis" to read -- N is --

Column 14, Line 15: Please correct "$10^4$" to read -- $10^{-4}$ --

Column 15, Line 3: Please correct "2" to read -- $\lambda$ --

Column 16, Line 24: Please correct "2" to read -- $\lambda$ --

Signed and Sealed this
First Day of September, 2020

Andrei Iancu
*Director of the United States Patent and Trademark Office*